United States Patent [19]
Joly et al.

[11] Patent Number: 6,005,156
[45] Date of Patent: Dec. 21, 1999

[54] PARA-XYLENE SEPARATION PROCESS COMPRISING PRETREATMENT BY SELECTIVE HYDROGENATION AND BY ACTIVATED CLAY

[75] Inventors: Jean François Joly, Lyon; Charles Cameron, Paris; Pierre Renard, Saint non la Breteche; Françoise Montecot, les Clayes sous Bois; Jean Cosyns, Maule; Gérard Leger, Caluire, all of France

[73] Assignee: Institut Francais du Petrole, Rueil Malmaison, France

[21] Appl. No.: 08/894,408
[22] PCT Filed: Feb. 14, 1996
[86] PCT No.: PCT/FR96/00238
§ 371 Date: Jan. 27, 1998
§ 102(e) Date: Jan. 27, 1998
[87] PCT Pub. No.: WO96/26170
PCT Pub. Date: Aug. 29, 1996

[30] Foreign Application Priority Data

Feb. 21, 1995 [FR] France .................................. 95 02082

[51] Int. Cl.$^6$ ....................................... C07C 7/00
[52] U.S. Cl. .......................... 585/805; 585/319; 585/254; 585/479; 585/258; 585/253; 585/260
[58] Field of Search ..................... 585/805, 319, 585/254, 479, 258, 253; 208/260

[56] References Cited

U.S. PATENT DOCUMENTS

| | | | |
|---|---|---|---|
| 3,548,017 | 12/1970 | Hebert et al. ........................... | 585/478 |
| 3,835,037 | 9/1974 | Fairweather et al. .................... | 208/260 |
| 4,118,429 | 10/1978 | Fritsch et al. ............................ | 585/254 |
| 4,224,141 | 9/1980 | Morrison et al. ........................ | 208/134 |
| 5,284,992 | 2/1994 | Hotier et al. ............................. | 585/805 |
| 5,329,061 | 7/1994 | Swift ........................................ | 585/805 |
| 5,417,844 | 5/1995 | Boitiaux et al. ......................... | 208/143 |
| 5,417,957 | 5/1995 | Coe et al. ................................. | 423/700 |
| 5,516,955 | 5/1996 | Gentry ..................................... | 585/477 |
| 5,609,751 | 3/1997 | Wall ......................................... | 208/133 |
| 5,629,467 | 5/1997 | Hotier et al. ............................. | 585/805 |
| 5,763,714 | 6/1998 | Hickey et al. ........................... | 585/253 |

*Primary Examiner*—Walter D. Griffin
*Attorney, Agent, or Firm*—Millen, White, Zelano & Branigan, P.C.

[57] ABSTRACT

In a process for the separation of p-xylene from a feed to be treated containing a mixture of xylenes and olefinic impurities, at least a portion of the feed is circulated in an enrichment zone (14) to enrich a first fraction (15) in p-xylene and provide a second fraction (18) which is depleted in p-xylene. The second fraction is circulated in an isomerisation zone (19) and an isomerate (20) is recovered which is recycled to the enrichment zone. At least a portion of the feed to be treated, the isomerate, or a mixture thereof is circulated in at least one selective hydrogenation zone (3) to partially remove the olefinic impurities and thereafter in at least one clay tretment zone (8) to remove additional olefinic impurities. An effluent is recovered which is sent to the enrichment zone.

25 Claims, 6 Drawing Sheets

PARA-XYLENE SEPARATION PROCESS COMPRISING PRETREATMENT BY SELECTIVE HYDROGENATION AND BY ACTIVATED CLAY

BACKGROUND OF THE INVENTION

The present invention concerns a novel sequence of catalytic processes, purification processes and separation processes for the production of high purity aromatic compounds such as benzene, ortho-xylene and para-xylene.

It also concerns a novel process for the treatment of hydrocarbon cuts which are rich in aromatic compounds, more particularly a process for the elimination of diolefins and the reduction and possible elimination of olefins from mixtures of aromatic compound-rich hydrocarbons using a hydrogenation reaction by means of particular catalysts.

More particularly, it concerns the production of very pure para-xylene, in particular for the synthesis of terephthalic acid which is mainly used in the textile industry.

Mixtures of aromatic compound-rich hydrocarbons are used in petrochemical plants which produce benzene, toluene, ethylbenzene, meta-xylene, ortho-xylene, para-xylene, ethylbenzene and styrene after various separation and purification treatments.

The sources of aromatic compound-rich cuts containing different concentrations of diolefins and olefins are generally: distillation processes for crude hydrocarbons such as crude oil, condensed natural gas, coal; thermal processes such as steam cracking of naphtha; processes dedicated to the production of aromatics from light aliphatic cuts ($C_3$–$C_5$, more particularly $C_3$ and $C_3/C_4$), $C_6$ and $C_6/C_7$ aliphatics, and heavy naphtha cuts (>$C_6$ for various catalytic reforming processes); and processes for transforming aromatic products, such as processes for trans-alkylation and isomerisation of ortho- and meta-xylenes to para-xylene.

Catalytic reforming is the major process for producing mixtures which are rich in aromatic compounds. At first, catalytic reforming was carried out in two types of facilities, depending on whether it was to be used for refining or petrochemistry. Later on, this distinction, linked to the severity of the operating conditions, has become blurred.

Nowadays, in order to satisfy increased energy constraints, the industry is again seeking more specific processes. They thus use, for refining, catalytic reforming units which operate at high severity but which have greater operational stability and improved spirit yields, and for petrochemistry aromatic production (benzene, toluene and xylenes) is optimised by using a reactor which operates at low pressure.

The use of reformers operating at high severity is accompanied by an increase in the concentration of olefins and diolefins in the reformates. The bromine number of a stabilised reformate can reach a maximum value of over 7000 mg of bromine per 100 g of product for units operating at very low pressure. The presence of these olefins and diolefins is particularly prejudicial to aromatic separation processes. As an example, olefins and diolefins tend to polymerise in the solvents used for extraction. Purification treatments using natural silico aluminates, usually activated (for example attapulgite, bentonites and montmorillonites activated by treatment in the presence of acids) are currently used. Those purification materials are generally termed activated clays.

Purification treatments using activated clay have a number of problems, among them: a short lifetime (generally 4 to 6 months, sometimes as low as one month for feeds containing high concentrations of olefins, >0.6% by weight), low catalytic activity (hourly space velocities in the range 0.5 to 3 volumes of feed/volume of catalyst/hour), and great difficulty in purifying feeds containing more than 1.5% by weight of olefins and diolefins, which limits the operating severity of the reformer. Purification of the feed is accompanied by the production of high molecular weight compounds due to alkylation of the aromatics. These products must then be separated out. They cannot be regenerated economically and are thus eliminated in the waste with their toxic residual aromatic products.

Conventional schemes for the production of aromatic compounds containing 6 to 8 carbon atoms per molecule are complex. They comprise a succession of separation, purification and catalytic process steps. An aromatic plant for the production of para-xylene and ortho-xylene can be described as comprising at least the sequence of steps described above.

The source of aromatics, i.e., the stabilised reformate, is introduced into a separating column to produce a $C_7^-$ cut overhead which contains benzene and toluene, the column being currently termed a "deheptanizer". An aromatic $C_8^+$ cut is extracted from the bottom of the deheptanizer and purified by passage over at least one bed of activated clay. Purification is intended to eliminate the major portion of the olefins and diolefins from that $C_8^+$ cut. Since the lifetime of those activated clay beds is relatively short, two or more beds are positioned in parallel to allow a change from one to the other to enable discharge of the used clay without stopping the production of purified $C_8^+$.

Following the clay treatment, the aromatic $C_8^+$ cut is introduced into a separating column from which an aromatic $C_8$ cut is extracted overhead (xylene+ethylbenzene) and a heavy fraction containing ortho-xylene and compounds with a higher molecular weight than ortho-xylene is extracted from the bottom. Normally, a second separation step is carried out on the latter cut and ortho-xylene is recovered overhead from the second column while an aromatic $C_9^+$ cut is recovered from the bottom, from which the $C_9$ aromatics may be separated to produce, by transalkylation with benzene, an additional quantity of para-xylene and ortho-xylene.

The aromatic $C_8$ cut obtained overhead from the first column, which contains the three isomers of xylene (ortho-xylene, meta-xylene and para-xylene) plus ethylbenzene, is sent to a xylene separation unit which uses, for example, molecular sieves or a crystallization process, from which para-xylene and an aromatic $C_8$ cut are obtained. The latter is introduced into a catalytic isomerisation unit, possibly after addition of hydrogen, in which the xylenes and possibly ethylbenzene are isomerised to produce a $C_8$ aromatic mixture at close to thermodynamic equilibrium, which thus contains para-xylene. One isomerisation scheme is described in United States patent U.S. Pat. No. 4,224,141.

Following the isomerisation reactor, a column for separating the light $C_5^-$ fractions produced in the isomerisation reactor is generally used, followed by a further separating column from which a $C_8^+$ cut, containing $C_8$ aromatics close to thermodynamic equilibrium and heavy aromatic compounds from the transalkylation reactions of the isomerisation process, is recovered from the bottom. The aromatic $C_8^+$ cut may contain olefins and diolefins. This cut is thus normally treated on at least one activated clay bed before recycling it to the deheptanizer which treats the reformate. A scheme of this type is described in French patent application FR 94/15896 which also comprises a para-xylene enrichment process by selective adsorption or low temperature crystallization, a step of purification by crystallization with at least one high temperature stage, and an isomerisation process. This requires the use of at least two reactors and the waste clay becomes more and more of a problem for reasons of environmental pollution.

United States patent U.S. Pat. No. 4,118,429 describes a process for the hydrogenation of olefins in effluents from units for the isomerisation of aromatic compounds using a metal catalyst selected from the following metals: ruthenium, rhodium, palladium, osmium, iridium, platinum, or a mixture of those metals. The stated aim of that invention is to improve recovery of para-xylene on treatment with the adsorbent. The example indicates that an olefin-free effluent is obtained after treatment at 177° C. at a pressure of 9.7 bar, a space velocity of 3 $h^{-1}$ and using a catalyst composed of 0.375% by weight of platinum on alumina. The aromatic compound loss is not explained in the description of that invention; however, the loss is significant. In fact, the hydrogenation of xylene-rich cuts by metals from group VIII leads to a significant loss of xylenes in the form of dimethylcyclohexanes, as will be indicated below.

Further, the effluent still contains monoolefins which adversely affect downstream treatment, in particular molecular sieve adsorption.

SUMMARY OF THE INVENTION

The aim of the invention is to overcome the problems described above.

More precisely, the invention provides a process for the separation and recovery of p-xylene from a feed to be treated containing a mixture of xylenes, in which at least a portion of a feed containing a mixture of xylenes is circulated in a zone termed the enrichment zone (14) to enrich a first fraction (15) in p-xylene and to provide a second fraction (18) which is depleted in p-xylene, the second fraction being circulated in an isomerisation zone (19) and an isomerate (20) being recovered which is recycled to the enrichment zone, the process being characterized in that at least a portion selected front the group formed by the initial feed, the isomerate, and a mixture thereof, is circulated in at least one selective hydrogenation zone (3) in the presence of hydrogen then in at least one clay treatment zone (8), a step (5) for the separation of excess hydrogen being carried out in at least one separation zone before or after the clay treatment, and an effluent is recovered which is sent to the enrichment zone (14).

A number of variations are possible. In a first variation, the isomerate and the feed to be treated are hydrogenated in hydrogenation zone (3) then treated with clay (8) before or after separation of hydrogen (5) then the resulting effluent is sent to the enrichment zone (14).

In a second variation, the feed to be treated is hydrogenated in hydrogenation zone (3) then treated with clay (8) before or after separation of hydrogen (5), the isomerate (20) being recycled between the hydrogenation and clay treatment zones, and the effluent is recovered and sent to the enrichment zone (14).

In a third variation, the feed to be treated is hydrogenated in hydrogenation zone (3) then treated with clay before or after separation of hydrogen and the isomerate (20) is recycled downstream of the clay treatment zone (8) for the hydrogenated feed, the isomerate having been clay treated in a different treatment zone (24).

In a fourth variation, the isomerate is hydrogenated in hydrogenation zone (3) then clay treated (8) before or after hydrogen separation, and the feed to be treated, from which at least a portion of the diolefins has been eliminated, is introduced upstream of the enrichment zone (14).

The process of the present invention can purify mixtures of hydrocarbons which are rich in aromatic compounds and does not have the problems inherent in conventional treatments using only activated clay treatment as a purification system. The process of the present invention can purify a number of hydrocarbon feeds in which the concentration and nature of the aromatics can vary within a very wide range. Further, the process is not limited by the olefin and diolefin content of the feeds to be purified. Some advantages of the process are:

the possibility of treating feeds characterized by high olefin and diolefin concentrations, for example 0.1% to more than 3% by weight of olefins and advantageously less than 0.3% by weight of dienes;

the concentration of aromatic compounds in the hydrogenated effluents remains practically unchanged;

the absence of production of high molecular weight compounds during the hydrogenation step; the olefins may be transformed, and the diolefins are converted into paraffins;

the environmental burden is significantly reduced since the catalyst can be regenerated and non hydrogenated olefins are the least harmful to the downstream treatment processes. The lifetime of the activated clay is substantially prolonged, and quantity of discarded clays is thus much lower compared with conventional processes.

It has been shown, for example, that when a feed was treated in accordance with the process of the invention and the isomerate was recycled upstream of the clay treatment zone, only one clay treatment reactor was required which could even be circumvented during clay changing operations.

In accordance with one feature of the invention, $C_7^-$ can be separated simultaneously with separating the excess hydrogen resulting from the selective hydrogenation step.

In a further variation, separation is enhanced by carrying out the hydrogen separation step in a first separation zone, then separating the $C_7^-$ compounds in at least one further separation zone.

It is also possible to improve the separation of these compounds depending on the intended use of the intermediate cuts. Thus, hydrogen separation is carried out in a first separation zone, then the $C_5^-$ compounds are separated in a second separation zone, and the remaining $C_7^-$ compounds are separated in a third separation zone.

Hydrogen separation can also be carried out in a first separation zone, then the $C_4^-$ compounds are separated in a second separation zone, and the remaining $C_7^-$ compounds are separated in a third separation zone.

The separated hydrogen can be at least partially recycled to the selective hydrogenation zone.

These last three alternatives can advantageously recover substantially pure intermediate fractions, heptane cut, pentane cut, or butane cut, and in particular those which are free of diolefins or heavier products which could block the molecular sieves of the reactors.

Light compounds, in particular $C_7^-$ hydrocarbons being formed during the isomerisation step, can be separated after the isomerisation step, for example by distillation.

In general, the feed to be treated containing variable concentrations of diolefins and olefins is a crude reformate, a crude reformate from which at least a portion of the $C_3^-$ compounds has been eliminated, a crude reformate from which at least a portion of the $C_4^-$ compounds has been eliminated, a crude reformate from which at least a portion of the $C_5^-$ compounds have been eliminated, or a $C_8$ cut rich in aromatic compounds containing a major portion of xylenes, or mixtures thereof.

In a further feature of the invention, the effluent to be enriched is circulated in at least one distillation column termed a "rerun" column located at the inlet to the para-xylene enrichment zone to recover a mixture of xylenes and ethylbenzene and a mixture of heavy ortho-xylene products.

In a first variation, this enrichment zone is formed by at least one very low temperature crystallization zone which, after a separation step, produces a liquid (the second fraction) which is isomerised in the isomerisation zone, and crystals which are melted which form at least a portion of the first fraction.

In a particularly advantageous second variation, the para-xylene enrichment zone is formed by a selective adsorption zone containing a zeolitic adsorbent, the feed is selectively adsorbed in the presence of a desorption solvent, the first fraction which is enriched in para-xylene, and the second fraction which is depleted in para-xylene are recovered, the second fraction is isomerised in an isomerisation zone containing an isomerisation catalyst under conditions suitable for the production of an isomerate containing para-xylene and at least a portion of the isomerate is recycled to the adsorption zone.

In a further feature of the invention, the diolefins are selectively hydrogenated in the presence of a catalyst containing at least one element from group VIII into which sulphur has been introduced prior to the passage of the feed to be hydrogenated. The sulphur can be introduced by treating the catalyst with a sulphur-containing compound in the hydrogenation zone, or it can be introduced into the catalyst by means of a sulphur-containing agent prior to charging the catalyst into the hydrogenation zone.

More precisely, in the latter case, at least one sulphur-containing agent based on an organic compound containing sulphur can be incorporated into the catalyst prior to its use and prior to its activation by hydrogen.

The sulphur-containing agent can be selected from at least one thioether $R_1$—S—$R_1$, at least one thiol $R_1$—SH, at least one organic disulphide $R_1$—S—S—$R_2$ or HO—$R_1$—S—S—$R_2$—OH and at least one organic polysulphide $R_1$—(S)$_n$—$R_2$, the organic radicals $R_1$ and $R_2$ being identical or different, taken separately or in combination, and n is a whole number from 1 to 20.

Advantageously, this agent is selected from the group formed by hydrogen sulphide, dimethylsulphide, dimethyldisulphide or ditertiononylpolysulphide (TPS-37, Elf Atochem).

These sulphur-containing agents and their incorporation into the catalyst are described in French patent FR-A-2 664 610 and French patent application FR-95/00977, which are incorporated by reference.

Preferred catalysts contain at least one metal from the group formed by nickel, platinum and palladium, more particularly 0.1% to 1% by weight of platinum or palladium with respect to the support, or 5% to 70% by weight of nickel with respect to the support.

Generally, 0.05% to 10% of sulphur, expressed by weight with respect to the mass of the catalyst, is incorporated, more particularly 0.05% to 1% of sulphur when palladium is used, in particular when the quantity of diolefins to be extracted from the feed is low.

The selective hydrogenation conditions are generally as follows:

temperature: 20° C. to 250° C., preferably 80° C. to 180° C.;

pressure: 4–50 bar, preferably 10 to 40 bar;

HSV: 0.2 to 25 h$^{-1}$, preferably 2 to 15 h$^{-1}$;

molar ratio: hydrogen/monoolefins+polyolefins and/or acetylenes: 0.3–100, preferably 1–50.

Under these conditions, conversion of the aromatic compounds in the feed is less than 0.15%, preferably less than 0.1%. Feeds which are suitable for use in the present invention have a bromine number of 10000 to 100 mg per 100 g of product, for example.

The process normally comprises at least one catalytic hydrogenation reactor in which the feed to be treated is mostly liquid at the reactor inlet. Preferably, at least 80% by weight of the feed is liquid at the reactor inlet.

Hydrogen and the feed to be treated are injected as an upflow or downflow into the reactor, which preferably comprises a fixed catalyst bed.

After hydrogenation, the diolefin conversion is generally more than 75%, usually more than 90%. In contrast, the monoolefin conversion is substantially less (15% to 40%, for example).

Activated clay treatment is thus generally carried out under the conditions described in our French patent applications FR-94/15896 and FR-94/15897 which are hereby incorporated by reference. As an example, the conditions for adsorption or elimination of undesirable compounds are as follows:

temperature: 100° C. to 300° C., organic 160° C. to 230° C.;

hourly space velocity: 1 to 8, preferably 1 to 4 (volume of feed per volume of clay per hour);

type of clay: activated natural aluminosilicates, for example clay with reference number F54, from Engelhard;

pressure: 3 to 100 bar, preferably 4 to 20 bar.

The xylene fraction, free of the major portion of impurities, can be enriched by selective adsorption on a molecular sieve as described in our patents, U.S. Pat. No. 5,284,992, hereby incorporated by reference, or by low temperature crystallization as described in United States patents U.S. Pat. No. 5,329,061 and U.S. Pat. No. 2,866,833, hereby incorporated by reference. The enriched fraction can then be purified in a purification zone by at least one high temperature crystallization step, preferably in a purification zone comprising at least two high temperature crystallization zones as described in the following French patent applications, which are incorporated by reference: FR 94/15896, FR 94/15897 and FR 95/00746.

At least a portion of the mother liquor resulting from the coldest stage of the purification zone can then be recycled to the inlet to the selective hydrogenation zone where it can be mixed with the initial feed and/or isomerate. In a further variation, it can be recycled to any point upstream of the enrichment zone, for example before or after the clay treatment reactor.

The invention will be better understood from FIGS. 1 to 6 which provide a schematic and non limiting illustration of a number of variations of the process. Components of the apparatus with well defined functions have the same reference numerals in all the figures.

DETAILED DESCRIPTION OF THE FIGURES

Figure 1:
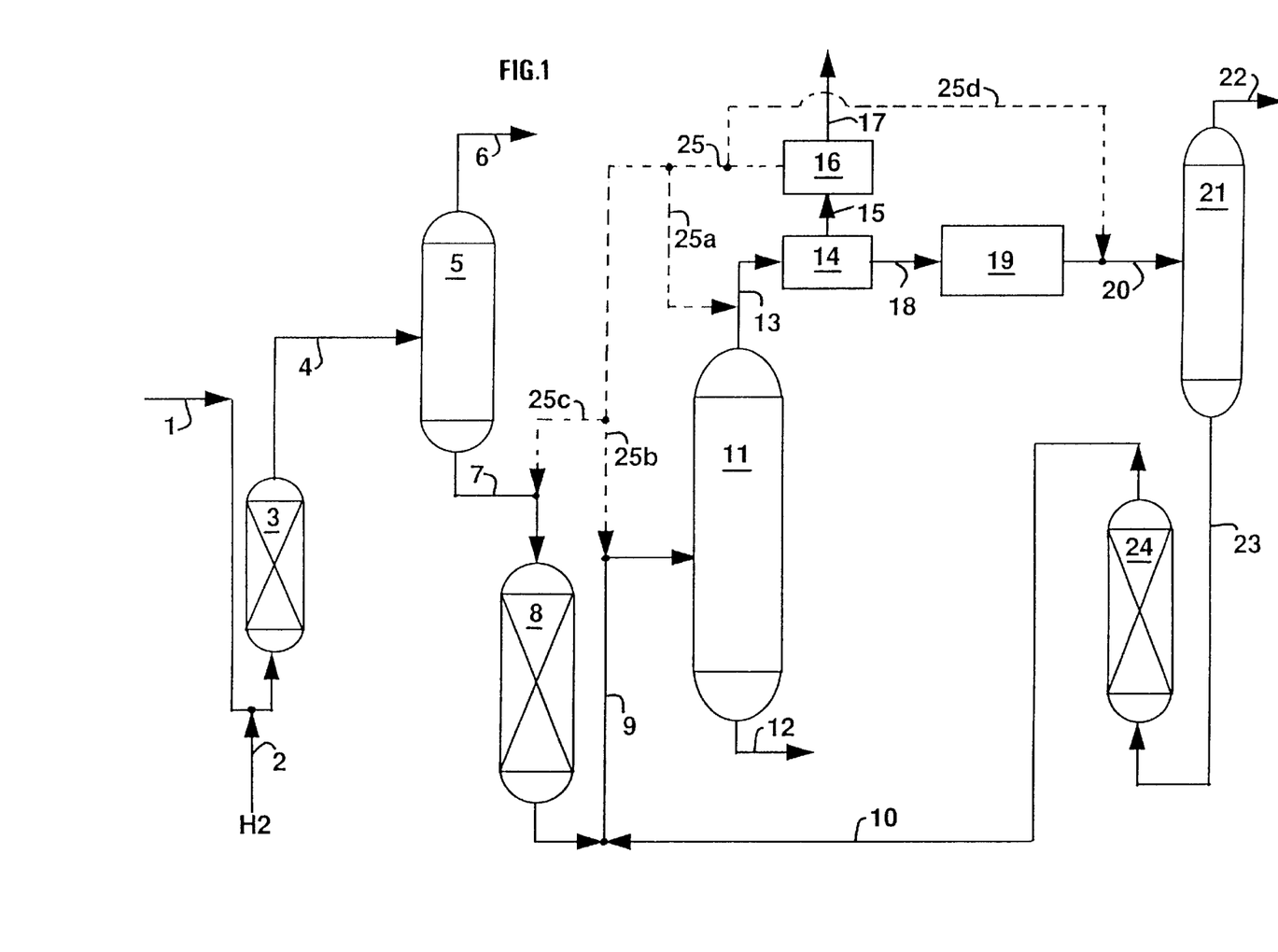
FIGS. 1–6 are schematic flowsheets of the invention.

In FIG. 1, the aromatic feed, for example a crude reformate, which has been freed of $C_3^-$ and $C_4^-$ hydrocarbons (not shown in the figure) is introduced via line 1, in the presence of hydrogen which may have been recycled via line 2 into a selective hydrogenation reactor 3 comprising a fixed bed of catalyst (transition alumina) containing 0.1% to 1% by weight with respect to the palladium support, which has been sulphurated ex-situ and contains 0.05% to 1% of sulphur (by weight with respect to the catalyst mass). The hydrogenated effluent containing substantially no more diolefins is sent via line 4 to a separator 5 (main deheptanizer) from which excess hydrogen and $C_7^-$ hydrocarbons of increased purity, such as benzene and toluene, are extracted via line 6. A liquid $C_8^+$ effluent (xylenes, ethylbenzene and $C_8^+$) is sent via line 7 from the bottom of separator 5 to at least one activated clay treatment reactor 8 (attapulgite, for example). At its exit, a liquid effluent is introduced via line 9 into a separator 11 from which orthoxylene and heavy $C_8^+$ hydrocarbons are extracted from the bottom via line 12. The ortho-xylene can optionally be separated overhead in a further separator which is not shown in the figure.

Line 13 recovers from the separator an overhead fraction containing mainly aromatic compounds containing 8 carbon atoms per molecule, xylenes and ethylbenzene, and introduces these into para-xylene enrichment zone 14, for example a selective adsorption zone using a molecular sieve operating as a simulated mobile bed, desorbed by toluene or para-diethylbenzene. Line 15 recovers an extract containing para-xylene which can be subsequently purified by at least one stage of high temperature crystallization, preferably two stages, between +10° C. and −25° C. A fraction which is depleted in para-xylene and free of solvent is sent via line 18 to an isomerisation zone 19 which may operate in the presence of hydrogen, from which an isomerate is recovered via line 20. This isomerate contains $C_5^-$ hydrocarbons, $C_7^-$ hydrocarbons and a $C_8^+$ fraction and is sent via line 20 to at least one separation zone 21 (for example two), not shown in the figure, one removing the $C_5^-$ hydrocarbons and another removing the $C_7^-$ hydrocarbons (secondary deheptanizer). Benzene and toluene are separated overhead from zone 21, via a line 22. An effluent containing xylenes, ethylbenzene and compounds containing more than 8 carbon atoms are recovered from the bottom via line 23 which introduces it into at least one clay treatment reactor 24. The isomerisation effluent treated with clay, free of the majority of olefins, is recycled via line 10 connected to line 9 to separator 11 upstream of adsorption zone 14.

After separating the solvent, the fraction which is enriched in para-xylene from selective adsorption zone 14 is introduced via line 15 into a purification zone which is a high temperature (for example +10° C. to −25° C.) crystallization zone comprising one or two stages. The suspension of crystals produced is separated by at least one centrifuge (not shown in the figure) and 99.9% pure crystals are collected via line 17. These para-xylene purification stages are described in our patent applications cited above. A mother liquor from the centrifuging step is recovered (that from the coldest crystallization stage when there are two) and is recycled either to the inlet to adsorption zone 14 via lines 25, 25a, or to the inlet to separation zone 11 via lines 25, 25b, or to the inlet to the activated clav reactor via Lines 25, 25c, or to the inlet to separator 21 via lines 25, 25d.

Figure 2:
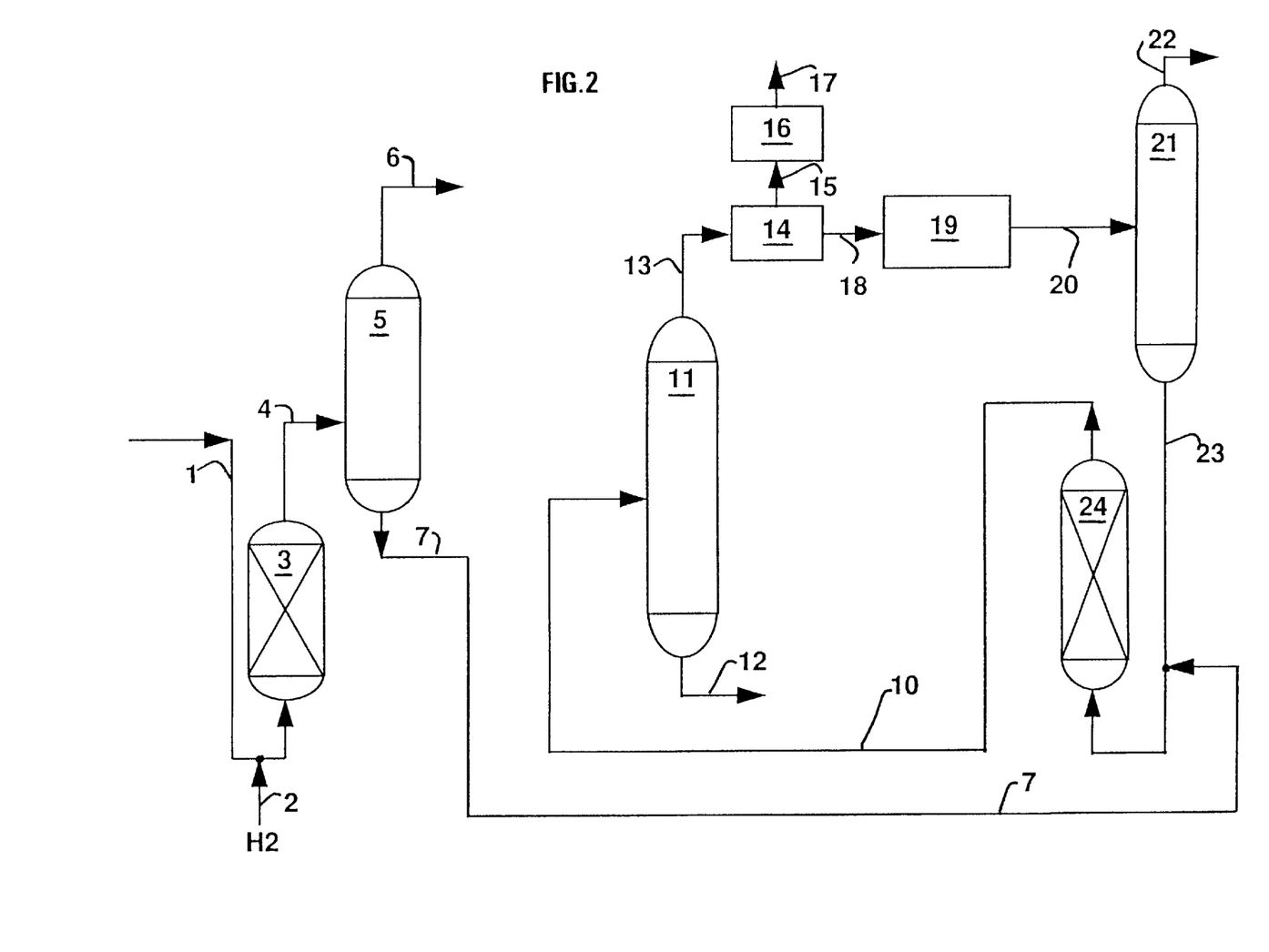

In FIG. 2, the same components have the same reference numerals as those of FIG. 1. In this figure, feed 1, selectively hydrogenated and free of excess hydrogen, i.e., the effluent from separator 5, is introduced via line 7 into clay treatment reactor 24. Isomerate is also introduced into this reactor via line 23, from which isomerate light compounds have been eliminated via line 22. The clay treated mixture is sent via line 10 to separator 11.

Figure 3:
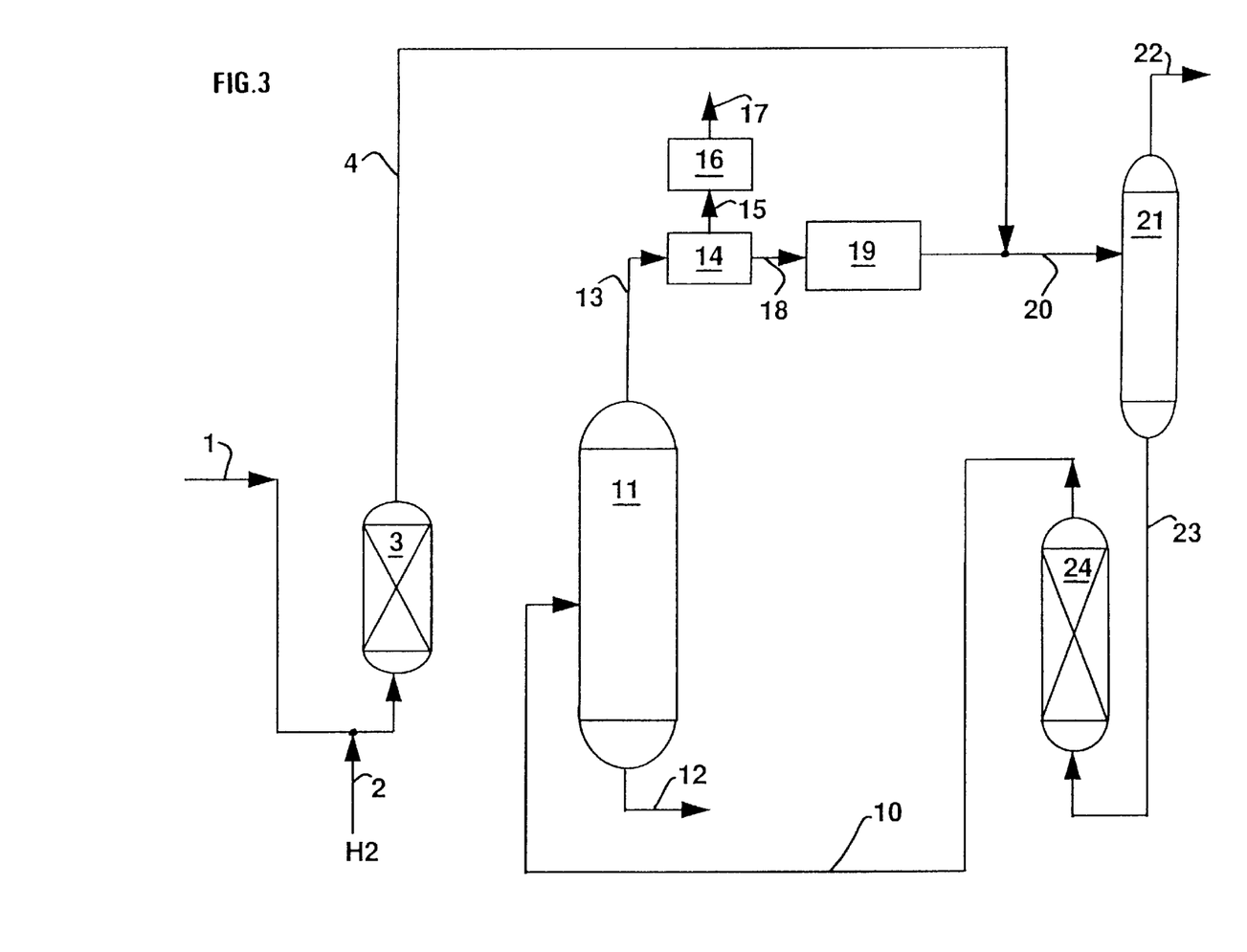

In FIG. 3, in which the same components have the same reference numerals as those of FIG. 1, the selectively hydrogenated feed is freed of excess hydrogen in the separator which also treats the crude isomerate. In other words, the hydrogenation effluent is introduced via line 4 into line 20 which conducts the isomerate to separator 21. Line 23 recovering heavy effluent from separator 21 feeds clay treatment reactor 24. The effluent from the clay reactor is introduced, as before, via line 10 into separator 11 which extracts the undesirable heavy compounds.

Figure 4:
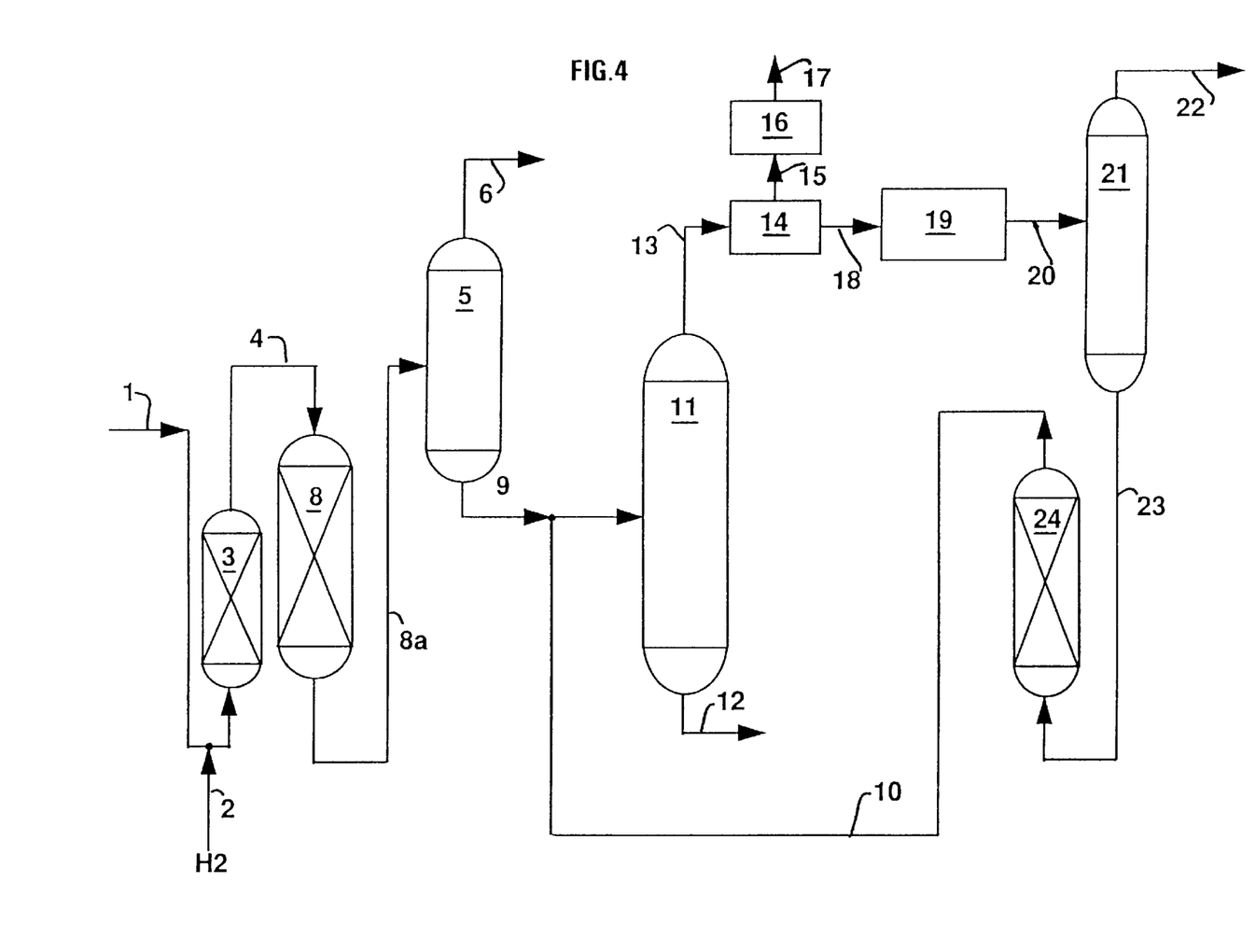

FIG. 4 is substantially the same as FIG. 1 except that the hydrogenation effluent via line 4 is introduced into clay treatment reactor 8 before being introduced via line 8a into separator 5 to extract light compounds and hydrogen.

The hydrogenated effluent, clay treated and free of light compounds, is then introduced via line 9 into separator 11 which also receives clay treated isomerate via line 10. The light effluent from separator 11 is treated in the same manner as that of FIG. 1.

Figure 5:
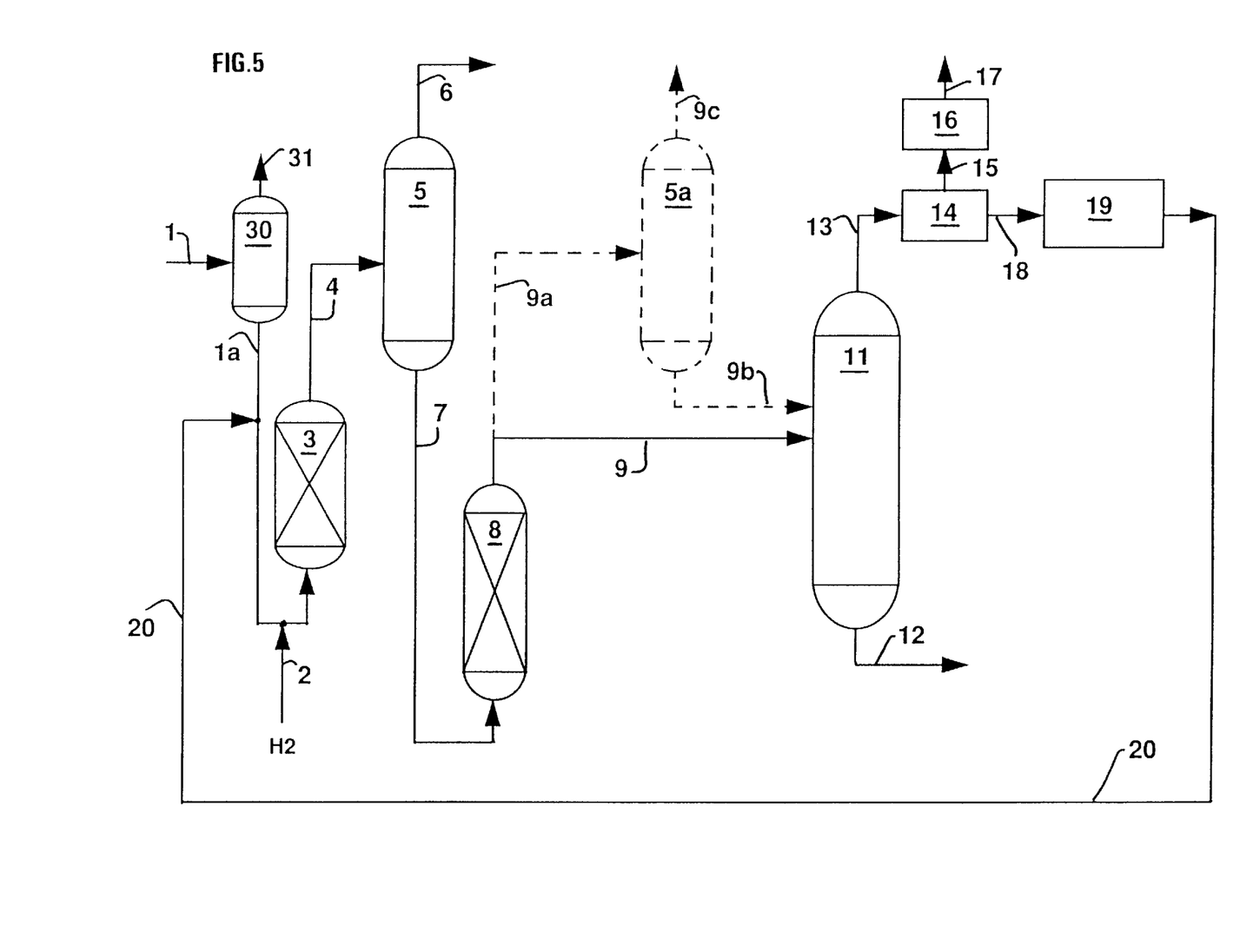
Figure 6:
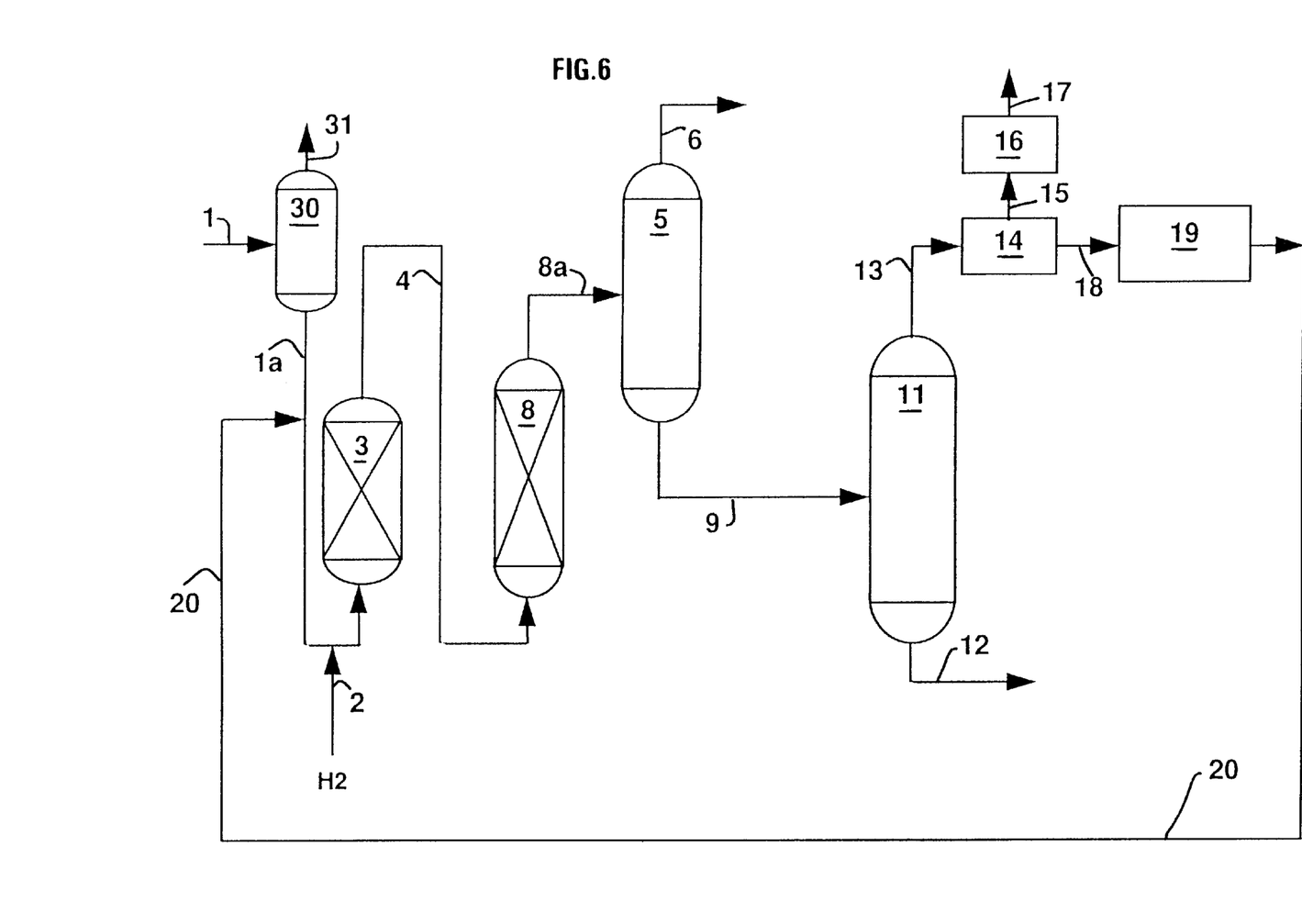

FIGS. 5 and 6 illustrate the cases where both the feed and isomerate are selectively hydrogenated, and freed of excess hydrogen before or after a clay treatment. Thus in FIG. 5, the feed introduced via line 1 is freed of $C_3^-$, $C_4^-$ and $C_5^-$ compounds in at least one separator 30. The effluent recovered via line 1a is mixed with crude isomerate supplied via line 20 and this mixture is introduced into selective hydrogenation reactor 3 which receives hydrogen via line 2. The hydrogenation effluent recovered via line 4 is freed of light $C_7^-$ compounds and excess hydrogen in separator 5 while the heaviest compounds are sent via line 7 to activated clay treatment reactors 8. The effluent from reactors 8, free of diolefins and the majority of monoolefins, is sent at least in part via line 9 to separator 11 to eliminate the heaviest compounds while the aromatic $C_8$ compounds recovered overhead are introduced into adsorption zone 14 from which a fraction which is enriched in para-xylene is recovered which can be purified by crystallization at 16. The fraction which is depleted in para-xylene is recovered via line 18 and sent to isomerisation zone 19. The crude isomerate is recovered via line 20 and recycled to selective hydrogenation reactor 3 as indicated above.

Preferably, $C_3^-$ compounds are separated in separator 30 and $C_4^-$ and $C_5^-$ compounds along with excess hydrogen are separated in separator 5. In this case, the effluent from the clay reactor is sent via line 9a to a further separator 5a (dotted line) which produces benzene and toluene overhead via line 9c and $C_8^+$ compounds from the bottom via line 9b, which supply separator 11. Since the hydrogen is separated upstream of clay reactor 8, better recovery of $C_8^+$ compounds is possible downstream of this reactor 8.

In FIG. 6, components carrying out the same functions are given the same reference numerals as those in FIGS. 1 to 5. The same arrangement as that shown in FIG. 5 is used, except that separator 5 for separating hydrogen and light $C_7^-$ compounds is located between the clay treatment reactor and separator 11. Thus the hydrogenated effluent which has been clay treated is recovered from reactor 8 via line 8a which conducts it to separator 5 from which hydrogen in particular is eliminated, and the heavier $C_8^+$ effluent is introduced via line 9 into separator 11 from which heavy $C_9^+$ compounds and possibly ortho-xylene are extracted.

We claim:

1. In a process for the separation and recovery of p-xylene from an initial feed to be treated containing a mixture of xylenes containing olefinic impurities comprising mono and diolefins, said process comprising circulating at least a portion of a feed containing a mixture of xylenes in an enrichment zone (14) to enrich a first fraction (15) in p-xylene and to provide a second fraction (18) depleted in p-xylene and containing said olefinic impurities; circulating said second fraction in an isomerization zone (19); recovering an isomerate (20) and recycling said isomerate to the enrichment zone, the improvement comprising circulating at least a portion of the initial feed, the isomerate or a mixture thereof, in at least one selective hydrogenation zone (3) in the presence of hydrogen under such conditions so as to hydrogenate only a portion of said olefinic impurities; circulating the resultant hydrogenated stream in at least one clay treatment zone (8) to remove more of said olefinic impurities from the hydrogenated stream, separating excess hydrogen in at least one separation zone (5) before or after said clay treatment, recovering an effluent resulting from the clay treatment, and passing said effluent to the enrichment zone (14).

2. A process according to claim 1, in which said mixture of the isomerate and the feed to be treated are hydrogenated in the hydrogenation zone (3) then treated with clay (8) before or after separation of hydrogen (5) and then the resulting effluenrt is sent to the enrichment zone (14).

3. A process according to claim 1, in which the feed to be treated is hydrogenated in the hydrogenation zone (3) then treated with clay (8) before or after separation of hydrogen (5), the isomerate (20) is recycled downstream of said hydrogenation zone to a clay treatment zone, and the isomerate effluent is recovered and sent to the enrichment zone (14).

4. A process according to claim 1, in which the feed to be treated is hydrogenated in the hydrogenation zone (3) then treated with clay in clay treatment zone (8) before or after separation of hydrogen; the isomerate (20) is recycled downstream of the clay treatment zone (8) and is treated in a different slay treatment zone (24).

5. A process according to claim 1, in which the isorterate (20) is hydrogenated in the hydrogenation zone (3) then clay treated (8) before or after hydrogen separation.

6. A process according to claim 1, characterized in that in said separation zone, hydrogen separation is carried out simultaneously with separation of $C_7^-$ compounds.

7. A process according to claim 1, in which hydrogen separation is carried out in a first separation zone, then $C_7^-$ compounds are separated in at least one further separation zone.

8. A process according to claim 1, in which hydrogen separation is carried out in a first separation zone, then $C_5^-$ compounds are separated in a second separation zone, and remaining $C_7^-$ compounds are separated in a third separation zone.

9. A process according to claim 1, in which hydrogen separation is carried out in a first separation zone, then $C_4^-$ compounds are separated in a second separation zone, and remaining $C_7^-$ compounds are separated in a third separation zone.

10. A process according to claim 1 in which separation of $C_7^-$ compounds is carried out in a separation zone downstream of the isomerisation zone (19) and upstream of the clay treatment zone.

11. A process according to claim 1, in which the feed to be treated is selected from the group consisting of a crude reformate, a crude reformate from which at least a portion of $C_3^-$ compounds has been eliminated, a crude reformate from which at least a portion of $C_4^-$ compounds has been eliminated, a crude reformate from which at least a portion of $C_5^-$ compounds have been eliminated, or a $C_8$ cut rich in aromatic compounds containing a major portion of xylenes, or mixtures thereof.

12. A process according to claim 1, in which the effluent to be enriched is circulated in at least one separator (11) located at the inlet to the enrichment zone.

13. A process according to claim 1, in which the paraxylene enrichment zone is formed by at least one crystallization zone which, after a separation step, produces a liquid being said second fraction which is isomerised in the isomerisation zone, and crystals which are melted form at least a portion of the first fraction.

14. A process according to claim 1, in which the paraxylene enrichment zone is formed by a selective adsorption zone containing a zeolitic adsorbent, the feed is selectively adsorbed in the presence of a desorption solvent, the first fraction, which is enriched in para-xylene, and the second fraction, which is depleted in para-xylene, are recovered, the second fraction is isomerised in the isomerisation zone which contains an isomerisation catalyst under conditions suitable for the production of an isomerate containing para-xylene, and at least a portion of the isomerate is recycled to the adsorption zone.

15. A process according to claim 1, in which selective hydrogenation is carried out in the presence of a catalyst containing at least one element from group VIII into which sulphur has been introduced prior to the passage of the feed to be hydrogenated.

16. A process according to claim 15, in which sulphur is introduced by treating the catalyst with a sulphur-containing agent in the hydrogenation zone.

17. A process according to claim 15, in which sulphur is introduced into the catalyst by means of a sulphur-containing agent introduced prior to charging said catalyst into the hydrogenation zone.

18. A process according to claim 17, in which at least one sulphur-containing agent based on an organic compound containing sulphur is incorporated into the catalyst prior to its use and prior to its activation by hydrogen.

19. A process according to any one of claim 15, in which the catalyst contains 0.1% to 1% by weight with respect to the support of palladium, said catalyst having been treated with said sulphur-containing agent before activation to introduce 0.05% to 1% by weight with respect to the mass of sulphur.

20. A process according to claim 1, wherein the initial feed has a bromine number of 1000 to 100 mg per 100 g of feed.

21. A process according to claim 20, wherein after said hydrogenation, the diolefin conversion is more than 75% and the mono olefin conversion is 15 to 40%.

22. A process according to claim 1, wherein after said hydrogenation, the diolefin conversion is more than 75% and the mono olefin conversion is 15 to 40%.

23. A process according to claim 21, wherein after said hydrogenation, aromatic compounds in the initial feed are converted to an extent of less than 0.15%.

24. A process according to claim 21, wherein after said hydrogenation, aromatic compounds in the initial feed are converted to an extent of less than 0.1%.

25. A process according to claim 20, wherein after said hydrogenation, the diolefin conversion is more than 90% and the mono olefin conversion is 15 to 40%.

* * * * *